United States Patent [19]

Bywater

[11] 4,164,568

[45] Aug. 14, 1979

[54] ORAL SCOUR FORMULATIONS WITH CITRATE

[75] Inventor: Robert J. Bywater, Tadworth, England

[73] Assignee: Beechamgroup Limited, Great Britain

[21] Appl. No.: 776,536

[22] Filed: Mar. 11, 1977

[30] Foreign Application Priority Data

Mar. 27, 1976 [GB] United Kingdom ............... 12417/76
Mar. 27, 1976 [GB] United Kingdom ............... 12418/76

[51] Int. Cl.² ................ A61K 33/14; A61K 31/70; A61K 31/19; A61K 31/195
[52] U.S. Cl. ................... 424/153; 424/180; 424/317; 424/319
[58] Field of Search ............... 424/153, 180, 317, 319

[56] References Cited

U.S. PATENT DOCUMENTS

| | | | |
|---|---|---|---|
| 2,333,950 | 11/1943 | Olsen et al. ........................... | 424/180 |
| 3,080,234 | 3/1963 | Jarowski ............................... | 424/319 |
| 3,337,404 | 8/1967 | Polli et al. ............................ | 424/153 |
| 3,360,434 | 12/1967 | Udenfriend et al. ................. | 424/319 |
| 3,362,879 | 1/1968 | Udenfriend et al. ................. | 424/319 |
| 3,743,744 | 7/1973 | O'Donovan .......................... | 424/317 |
| 3,898,328 | 8/1975 | Beigler et al. ........................ | 424/153 |
| 3,928,574 | 12/1975 | Philips ................................... | 424/153 |
| 4,042,684 | 8/1977 | Kahm .................................... | 424/153 |

OTHER PUBLICATIONS

Current Therapy-Ed.-H.F. Conn.-1977, pp. 416-417.

*Primary Examiner*—Albert T. Meyers
*Assistant Examiner*—D. W. Robinson
*Attorney, Agent, or Firm*—Jacobs & Jacobs

[57] ABSTRACT

A veterinary composition comprising 40 to 80% of an actively absorbed monosaccharide, 7.5 to 30% of an actively absorbed naturally occurring amino acid, and 0.5 to 10% of an agent which is citric acid or a salt thereof; except that when the agent is a salt of citric acid, then the amino acid represents no more than 13% of the composition; are useful in the treatment of diarrhoea in animals such as calves.

23 Claims, No Drawings

ORAL SCOUR FORMULATIONS WITH CITRATE

The present invention relates to veterinary compositions useful for treating diarrhoea (e.g. scours) in domestic animals and to the use of such compositions in the treatment of diarrhoea by rehydration.

A common and highly debilitating disease affecting young domestic animals such as calves and piglets is diarrhoea. Diarrhoea causes severe dehydration which in turn causes a significant weight loss in the animal and can in severe cases lead to death. It is believed that often the diarrhoea symptoms are caused by a toxin or toxins of bacterial origin so that one method for the treatment of diarrhoea is the administration of antibacterial agents. Considerable success can be achieved by using such anti-bacterial agents as ampicillin or amoxycillin but there are occasions when an alternative therapy is required. Recently U.S. Pat. No: 3,898,328 disclosed that compositions containing glycine, glucose and electrolytes are effective in the treatment of scours by bringing about a rehydration of the scouring animal.

A distinct class of compositions has now been discovered which combine effectiveness in diarrhoea (e.g. scours) treatment with ease of formulation, palatability and useful stability.

Accordingly the present invention provides a veterinary composition comprising 40 to 80% of an actively absorbed mono-saccharide, 7.5 to 30% of an actively absorbed naturally occurring amino acid, and 0.5 to 10% of an agent which is citric acid or a salt thereof; except that when the agent is a salt of citric acid, then the amino acid represents no more than 13% of the composition.

All percentages used herein are calculated on a weight/total weight basis.

Active absorption (or active transport) is well known to the skilled man, as are the monosaccharides and amino acids which are actively absorbed. In this regard the reader is referred to standard text books such as 'Medicinal Physiology' by Guyton (published by W. B. Saunders and Company) 4th Edition pages 769 to 771. Of course whether or not a particular monosaccharide or amino acid is actively absorbed may also readily be determined by experiment as for example described in Wilson T. H. 1962 Intestinal Absorption (Saunders, Philadelphia).

To be actively absorbed, monosaccharides must have (a) at least six carbon atoms in their chain, (b) a D-pyranose ring structure and (c) an intact hydroxyl group at carbon 2. Thus suitable examples of monosaccharides for use in this invention include the naturally occurring D-pyranoses such as glucose and galactose. Other examples of suitable monosaccharides include naturally occurring D-pyranoses that have been chemically modified whilst retaining the necessary structural features (a), (b) and (c). Examples of such modified monosaccharides include $C_{2-7}$ acylated and $C_{1-4}$ alkylated derivatives, such as acetyl, methyl, ethyl and n- and iso-propyl derivatives. Specific examples include α-methyl glucoside, 3-0-methyl glucose and 6-deoxygalactose.

Preferably the monosaccharide will be glucose or galactose. The monosaccharide of choice for use in this invention is glucose (e.g. dextrose). The stability of the resultant composition is enhanced if the monosaccharide used is anhydrous, for example anhydrous glucose.

Suitable examples of actively absorbed naturally occurring amino acids include neutral amino acids such as glycine and alanine and basic amino acids such as arginine. Preferably the amino acid is glycine.

The veterinary compositions of the invention will normally contain 10 to 25% electrolytes. Suitable electrolytes for such inclusion include salts containing ions such as sodium, potassium, calcium, magnesium, chloride, phosphate, gluconate, sulphate, bicarbonate, carbonate and the like. Other favoured electrolytes for inclusion in the compositions include potassium dihydrogen phosphate, dipotassium hydrogen phosphate, tripotassium phosphate, potassium chloride and the like, with potassium dihydrogen phosphate being particularly suitable.

One particularly preferred electrolyte for inclusion in the composition of the invention is sodium chloride which will normally account for 7 to 20% of the composition, for example 10–16% of the composition.

The monosaccharide is defined as representing 40 to 80% of the composition. More suitably it will represent 50 to 75%, for example 60 to 75% of the composition. Often the monosaccharide will represent at least 65% of the composition. Similarly while the amino acid in the composition can represent 7.5 to 30% of the composition, more suitably it will represent 7.5 to 20% of the composition, for example 8 to 15% of the composition. 8 to 12% has been found to be a particularly suitable inclusion range for the amino acid.

One suitable veterinary composition comprises 40 to 80% of an actively absorbed monosaccharide, 7.5 to 30% of an actively absorbed naturally occurring amino acid, and 0.5 to 10% of citric acid.

The citric acid represents 0.5 to 10% of this composition. More suitably the citric acid will represent 0.5 to 5%, preferably 0.5 to 2%, for example 0.6 to 1.2% of the composition. Often the composition will contain both citruc acid and a salt thereof, but the combined citric acid and the salt thereof will not represent more than 10% of the composition. Suitable examples of such salts include sodium or potassium salts such as mono-, di- or tri-sodium, or mono-, di- or tri-potassium citrate. Often the composition will include 0.1 to 5% of a salt of citric acid, more suitably 0.1 to 0.5% of such a salt.

From the aforesaid it will be seen that one particularly suitable veterinary composition of the invention will comprise 50 to 75% glucose or galactose, 7.5 to 20% of glycine, alanine or arginine, 0.5 to 10% citric acid and 7 to 20% of sodium chloride.

More suitably, such compositions will contain 0.5 to 5% citric acid, and 0.1 to 5% of a salt of citric acid.

Preferably such compositions contain glucose as the monosaccharide and glycine as the amino acid.

Thus a particularly preferred composition of the invention comprises 60 to 75% glucose, 8 to 15% glycine, 0.5 to 2% citric acid, 0.1 to 0.5% of a salt of citric acid, and 10 to 16% sodium chloride. Such compositions often include 5 to 10% of potassium dihydrogen phosphate.

A second suitable veterinary composition comprises 40 to 80% of an actively absorbed monosaccharide, 7.5 to 13% of an actively absorbed naturally occurring amino acid, and 0.5 to 10% of a citrate salt.

The citrate salt represents 0.5 to 10% of this composition. More suitably the salt will represent 0.5 to 5%, preferably 0.5 to 2%, for example 0.6 to 1.2% of the composition. Suitable examples of citrate salts include sodium or potassium salts such as mono-, di- or trisodium, or mono-, di- or tri-potassium citrate.

From the aforesaid it will be seen that one particularly suitable veterinary composition of the invention will comprise 50 to 75% glucose or galactose, 7.5 to 13% of glycine, alanine or arginine, 0.5 to 10% of a citrate salt and 7 to 20% of sodium chloride.

More suitably, such compositions will contain 0.5 to 5% of a salt of citric acid.

Preferably such compositions contain glucose as the monosaccharide and glycine as the amino acid.

Thus a particularly preferred composition of the invention comprises 60 to 75% glucose, 8 to 12% glycine, 0.5 to 2% of a salt of citric acid, and 10 to 16% sodium chloride. Such compositions often include 5 to 10% of potassium dihydrogen phosphate.

These compositions suitably contain at least 65% monosaccharide.

If desired the compositions of this invention can contain other substances such as vitamins, minerals, buffers, excipients or the like in conventional manner.

In general the compositions of this invention will be in the form of a dry powder for example one which is readily soluble in water. However in an alternative aspect the compositions of this invention will comprise an aqueous solution containing dissolved therein the previously defined solutes in the previously defined relative proportions.

The powders of this invention may be prepared by mixing together the individual components in conventional manner. Once mixed the composition may be put into sachets or other conventional containers. It is frequently advantageous to separate the monosaccharide component from the other components of the composition. This can be effected by using double sachets or other double containers. In such cases components other than the monosaccharide can be mixed and filled into one half of the double sachet and the monosaccharide can be filled into the other half of the double sachet. In such form the compositions of the invention have been found to be particularly stable.

The composition of the invention will normally be administered to the diarrhoeic animal in the form of an aqueous solution, by the oral route. Such solutions may for example contain 20 to 45 g./liter of the composition, suitably 25 to 35 g./liter, for example 30 g./liter. In general calves will be adminstered from 2 to at least 4 liters per day of such solutions while piglets will normally be administered from a quarter to a one liter per day. The solutions may be administered ad libitum or in two to four or more equal doses per day or by any other similar conventional regime.

From a further aspect this invention provides a method of treating diarrhoea in domestic animals which method comprises administering to the animal suffering from diarrhoea a liquid composition of this invention.

It will be realised that in the treatment of severely scouring animals anti-bacterial agents may be administered in conjunction with the compositions of the invention. Examples of suitable anti-bacterial agents for such use include ampicillin, amoxycillin and tetracyclines.

The skilled man will realise that the effective absorption properties found with the liquid compositions of the invention will enable them to be used with advantage whenever liquid absorption by animals is a problem. For example the compositions may be used in treating the general dehydration found in post-operative conditions in animals such as dogs and cats. They may also be administered with advantage to stressed animals, such as recently purchased calves and the like. It is however believed that the compositions of the invention will be of the greatest use in the treatment of diarrhoea in calves.

The following Examples illustrate the invention:

EXAMPLE 1

1 kg. of the following composition was prepared by mixing together the ingredients in dry powder form:

| | |
|---|---|
| Glycine | : 10.3% |
| Dextrose (anhydrous) | : 67.6 |
| Sodium Chloride | : 14.3 |
| Potassium Dihydrogen Phosphate | : 6.8 |
| Citric Acid | : 0.8 |
| Tri-potassium Citrate | : 0.2 |

60g. of the composition was then dissolved in 2 liters of water.

EXAMPLE 2

The following composition was prepared by a method analogous to that of Example 1:

| | |
|---|---|
| Glycine | : 10% |
| Dextrose (anhydrous) | : 72 |
| Sodium Chloride | : 10 |
| Citric Acid | : 5 |
| Tri-potassium Citrate | : 3 |

60g. of the composition was then dissolved in 2 liters of water.

EXAMPLE 3

For storage, the composition according to Example 1 was prepared in the same manner, but the dextrose (676g.) was filled into one container and the remaining ingredients (324g.) were filled into a second container.

EXAMPLE 4

By way of comparison, acute absorption studies were carried out on the composition of Example 1, hereinafter referred to as composition J, and a composition X:

| | w/w % |
|---|---|
| Sodium Chloride | 11.6 |
| Calcium Gluconate | 2.2 |
| Magnesium Sulfate | 0.6 |
| Monopotassium Phosphate | 8.7 |
| Glycine | 21.2 |
| Dextrose, anhydrous | 55.7 |

Composition X corresponds to Formulation 1 of Example 2 of U.S. Pat. No: 3,898,328. Composition J and Composition X were made up into isotonic aqueous solutions of approximately 300 milliosmoles/kg.. Isotonic Saline was used as a control.

The method used was to anaesthetise scouring calves, and identify points along the small intestine at about 10%, 30%, 50%, 70% and 90% of the distance from the pyloric sphincter to the ileocaecal valve. At each of these points, a series of short lengths of intestine were isolated by ligatures. Solutions under investigation were injected into these loops and the water movement followed by measuring changes in phenol red concentration.

The results obtained were as shown in the Table below:

| % Distance Pyloric Sphincter to the Ileo-caecal valve | Composition | Water Absorbed ml/cm/30 min (mean of seven tests) | Stan. Dev. |
|---|---|---|---|
| 10 | Saline | − 0.083 | ∓ 0.023 |
|  | X | − 0.016 | ± 0.019 |
|  | J | + 0.078 | ± 0.012 |
| 30 | Saline | − 0.007 | ± 0.020 |
|  | X | + 0.036 | ± 0.024 |
|  | J | + 0.070 | ± 0.022 |
| 50 | Saline | 0.031 | ± 0.020 |
|  | X | 0.079 | ± 0.032 |
|  | J | 0.146 | ± 0.040 |
| 70 | Saline | 0.108 | ± 0.027 |
|  | X | 0.085 | ± 0.036 |
|  | J | 0.128 | ± 0.007 |
| 90 | Saline | 0.099 | ± 0.038 |
|  | X | 0.129 | ± 0.032 |
|  | J | 0.145 | ± 0.034 |

These results shown that absorption of water by the scouring calves from composition J is significantly more rapid than from saline ($p<0.01$) or from composition X ($p<0.05$, analysis of variance).

EXAMPLE 5

1 kg. of the following composition was prepared by mixing together the ingredients in dry powder form:

| Glycine | 10.3% |
|---|---|
| Dextrose (anhydrous) | 67.6 |
| Sodium Chloride | 14.3 |
| Potassium Dihydrogen Phosphate | 6.8 |
| Tri-potassium Citrate | 1.0 |

60g. of the composition was then dissolved in 2 liters of water.

EXAMPLE 6

The following composition was prepared by a method analogous to that of Example 5:

| Glycine | 10% |
|---|---|
| Dextrose (anhydrous) | 72 |
| Sodium Chloride | 10 |
| Tri-potassium Citrate | 8 |

60g. of this composition was then dissolved in 2 liters of water.

EXAMPLE 17

For storage, the composition according to Example 5 was prepared in the same manner, but the dextrose (676g.) was filled into one container and the remaining ingredients (324 g.) were filled into a second container.

EXAMPLE 8

To 60g. of a composition prepared according to Example 1 was added 400mg. of amoxycillin.

EXAMPLE 9

1 kg. of each of the following compositions D, I and G were prepared by mixing together the ingredients in dry powder form:

|  | D | I | G |
|---|---|---|---|
|  | % | % | % |
| NaCl | 31.33 | 14.8 | 15 |
| Glucose | 50.5 | 66.87 | 61 |
| Glycine | 10.11 | 9.39 | 12 |
| Citric acid | 3.00 | 1.33 | 3 |
| $K_3$ citrate | 5.06 | 1.23 | 3 |
| $KH_2PO_4$ | — | 6.38 | 6 |

What we claim is:

1. A veterinary composition useful for treating diarrhoea in animals which comprises 40–80% of an actively absorbed monosaccharide, 7.5–30% of an actively absorbed, naturally occcurring amino acid, 0.5–5% of citric acid and 0.1–5% of a non-toxic salt of citric acid.

2. A veterinary composition according to claim 1 dissolved in an aqueous carrier suitable for veterinary admministration.

3. A veterinary composition according to claim 1 wherein the amount of the nontoxic salt of citric acid is from 0.1–0.5%.

4. A veterinary composition according to claim 1 which comprises 50–75% of an actively absorbed monosaccharide, 7.5–20% of an actively absorbed, naturally occurring amino acid, 0.5–5% of citric acid, 0.1–5% of a nontoxic salt of citric acid and 7–20% of sodium chloride.

5. A veterinary composition according to claim 1 which comprises 60–75% of an actively absorbed monosaccharide, 8–15% of an actively absorbed, naturally occurring amino acid, 0.5–2% of citric acid, 0.1–5% of a nontoxic salt of citric acid and 10–16% of sodium chloride.

6. A veterinary composition according to claim 5 which additionally contains 5–10% of potassium dihydrogen phosphate.

7. A veterinary composition according to claim 2 wherein the monosaccharide is glucose.

8. A veterinary composition according to claim 2 wherein the amount of monosaccharide is at least 65% of the composition.

9. A veterinary composition according to claim 2 wherein the amino acid is glycine.

10. A veterinary composition according to claim 2 wherein the amino acid is 8–12% of the composition.

11. A veterinary composition according to claim 2 which additionally contains an antibacterially effective amount of an antibacterial agent.

12. A stable veterinary composition according to claim 2 in oral administration form.

13. A method of treating diarrhoea in animals which comprises orally administering to an animal in need thereof a therapeutically effective amount of a composition which comprises 40–80% of an actively absorbed monosaccharide, 7.5–30% of an actively absorbed, naturally occurring amino acid, 0.5–5% of citric acid and 0.1–5% of a nontoxic salt of citric acid.

14. A method according to claim 13 wherein the composition is dissolved in an aqueous carrier suitable for veterinary administration.

15. A method according to claim 13 wherein the amount of the nontoxic salt of citric acid is from 0.1–0.5%.

16. A method according to claim 13 wherein the composition comprises 50–75% of an actively absorbed monosaccharide, 7.5–20% of an actively absorbed, naturally occurring amino acid, 0.5–5% of citric acid, 0.1–5% of a nontoxic salt of citric acid and 7–20% of sodium chloride.

17. A method according to claim 13 wherein the composition comprises 60–75% of an actively absorbed monosaccharide, 8–15% of an actively absorbed, naturally occurring amino acid, 0.5–2% of citric acid, 0.1–0.5% of a nontoxic salt of citric acid and 10–16% of sodium chloride.

18. A method according to claim 17 wherein the composition additionally contains 5–10% of potassium dihydrogen phosphate.

19. A method according to claim 14 wherein the monosaccharide is glucose.

20. A method according to claim 14 wherein the amount of monosaccharide is at least 65% of the composition.

21. A method according to claim 14 wherein the amino acid is glycine.

22. A method according to claim 14 wherein the amino acid is 8–12% of the composition.

23. A method according to claim 14 wherein the composition additionally contains an antibacterially effective amount of an antibacterial agent.

* * * * *